(12) United States Patent
Anantaneni et al.

(10) Patent No.: US 9,834,509 B2
(45) Date of Patent: Dec. 5, 2017

(54) METAL-CATALYZED OXIDATIVE COUPLING OF THIOLS

(71) Applicant: Ecolab USA Inc., St. Paul, MN (US)

(72) Inventors: Prakasa Rao Anantaneni, Richmond, TX (US); Ryan M. Harrington, Houston, TX (US); Boyd Laurent, Pearland, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/228,364

(22) Filed: Aug. 4, 2016

(65) Prior Publication Data

US 2017/0036998 A1 Feb. 9, 2017

Related U.S. Application Data

(60) Provisional application No. 62/201,322, filed on Aug. 5, 2015.

(51) Int. Cl.
*C07C 327/00* (2006.01)
*C07C 319/24* (2006.01)

(52) U.S. Cl.
CPC ................ *C07C 319/24* (2013.01)

(58) Field of Classification Search
CPC ... C07C 319/24; C07C 323/12; C07C 327/06; C07C 321/28; C07C 323/52; C07C 321/20; C07C 321/04; C07C 321/10; C07C 323/25; C07C 323/33
See application file for complete search history.

(56) References Cited

U.S. PATENT DOCUMENTS

| | | | | |
|---|---|---|---|---|
| 2,510,893 | A * | 6/1950 | Kleiman | ................ C07B 45/06 544/158 |
| 4,258,212 | A | 3/1981 | Schenk | |
| 4,288,627 | A | 9/1981 | Kubicek | |
| 4,295,979 | A | 10/1981 | Sharp et al. | |
| 4,307,236 | A * | 12/1981 | Zengel | ................ C07D 277/78 548/158 |
| 4,350,600 | A | 9/1982 | Sharp et al. | |
| 4,382,002 | A | 5/1983 | Walker et al. | |
| 4,450,102 | A | 5/1984 | Lindstrom et al. | |
| 4,721,813 | A | 1/1988 | Mark et al. | |
| H1147 | H | 3/1993 | Kennelley et al. | |
| 6,620,338 | B2 | 9/2003 | Fan et al. | |
| 6,645,399 | B2 | 11/2003 | Ahn et al. | |
| 7,423,183 | B2 | 9/2008 | Zeitler et al. | |
| 7,972,655 | B2 | 7/2011 | Abys et al. | |
| 9,238,588 | B2 | 1/2016 | Harrington et al. | |
| 2004/0170848 | A1 | 9/2004 | Ludwig et al. | |
| 2005/0079095 | A1 | 4/2005 | Crovetto et al. | |
| 2005/0183793 | A1 | 8/2005 | Kim et al. | |
| 2006/0142616 | A1 | 6/2006 | Zeitler et al. | |
| 2010/0175583 | A1 | 7/2010 | Roschmann et al. | |
| 2010/0197136 | A1 | 8/2010 | Shimada et al. | |
| 2015/0037202 | A1 | 2/2015 | Harrington et al. | |

FOREIGN PATENT DOCUMENTS

| | | |
|---|---|---|
| DE | 3008500 A1 | 9/1980 |
| WO | WO 00/34235 A1 | 6/2000 |
| WO | WO 00/75399 A2 | 12/2000 |
| WO | WO 2004/103956 A1 | 12/2004 |
| WO | WO 2015/017385 A2 | 2/2015 |

OTHER PUBLICATIONS

Korean Intellectual Property Office, International Search Report in International Patent Application No. PCT/US2014/048567, dated Jan. 28, 2015, 3 pp.
Korean Intellectual Property Office, Written Opinion in International Patent Application No. PCT/US2014/048567, dated Jan. 28, 2015, 9 pp.
Israel Patent Office, International Search Report in International Patent Application No. PCT/US2016/045464, dated Nov. 20, 2016, 5 pp.
Israel Patent Office, Written Opinion in International Patent Application No. PCT/US2016/045464, dated Nov. 20, 2016, 7 pp.

\* cited by examiner

*Primary Examiner* — Yevegeny Valenrod
*Assistant Examiner* — Blaine G Doletski
(74) *Attorney, Agent, or Firm* — Leydig, Voit & Mayer, Ltd.

(57) ABSTRACT

Disclosed are methods for preparing disulfide compounds through oxidative coupling of thiol compounds. Thiols are oxidized to the corresponding disulfide compound in high yield in presence of a base and a metal salt. The method uses low catalyst loadings and provides organic disulfide compounds with little to no byproducts.

20 Claims, No Drawings

METAL-CATALYZED OXIDATIVE COUPLING OF THIOLS

CROSS-REFERENCE TO RELATED APPLICATION

This patent application claims the benefit of U.S. Provisional Patent Application No. 62/201,322, filed Aug. 5, 2015, which is incorporated by reference in its entirety.

FIELD OF INVENTION

The invention relates to methods of oxidative coupling of thiol compounds to form disulfide compounds.

BACKGROUND OF THE INVENTION

Oxidative coupling is a common and efficient method used to convert thiol compounds into organic disulfide compounds. The reaction commonly involves coupling of two thiol molecules, and often employs oxidants such as hydrogen peroxide and molecular oxygen in conjunction with one or more catalysts to promote the coupling reaction. Aerobic oxidation is one of the most common methods used due to wide-availability of oxygen and the generation of water as the only theoretical reaction byproduct. A number of oxidation systems have been reported, but many are known to induce overoxidation to generate side products including thiosulfinates, thiosulfonates, and sulfonic acids. These overoxidation products not only reduce the quantity of disulfide obtained from the coupling reaction, but often necessitate additional synthetic operations including complicated workups and purifications. While thiols naturally undergo oxidative coupling in the presence of oxygen, a transition metal catalyst is often employed to obtain disulfides with lower temperatures and shorter reaction times. Many existing methods require the use of appreciable amounts of transition metal compound because the catalysts are often ineffective at promoting oxidative coupling at low catalyst loading. Thus, existing methods can be quite expensive due to the cost of the metal catalyst employed. Moreover, additional purification steps may be needed to remove the large quantities of metal impurities present in the disulfide product.

There is an ongoing need for efficient, cost-effective methods of producing organic disulfide compounds in high yield. The method should generate disulfides having low impurity content, and require little to no purification of the disulfide product.

BRIEF SUMMARY OF THE INVENTION

In an embodiment, the invention provides a method for producing a compound of formula (I)

(I)

or a salt thereof,
the method comprising contacting a thiol and a nickel salt, in the presence of a base, with oxygen; wherein each of $R^1$ and $R^2$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, or wherein $R^1$ and $R^2$ form a carbocyclic or heterocyclic ring; and wherein each of $R^1$ and $R^2$ is unsubstituted or substituted by one or more substituents.

In another embodiment, the invention provides a method for producing a compound of formula (II)

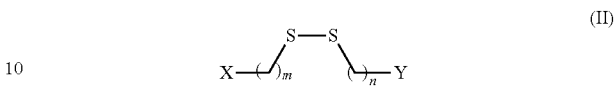

(II)

or a salt thereof,
the method comprising contacting a thiol and a nickel salt, in the presence of a base, with oxygen; wherein each of X and Y is the same or different and selected from the group consisting of —OH, —SH, —NH$_2$, halogen, —COOH, and —COOR; and wherein each of m and n is the same or different and is an integer from 1 to 16, and wherein R is $C_1$-$C_{18}$ alkyl or aryl. The compound of formula (II) may be unsubstituted or substituted with one or more substituents.

In another embodiment, the invention provides a method for producing a cyclic compound of formula (III)

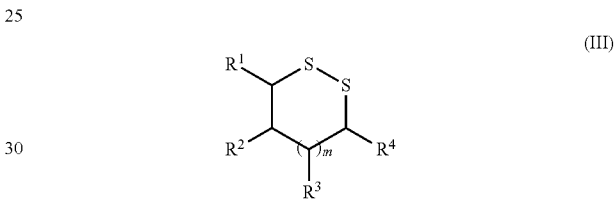

(III)

or a salt thereof,
the method comprising contacting a thiol and a nickel salt, in the presence of a base, with oxygen; wherein each of $R^1$, $R^2$, $R^3$, and $R^4$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, hydroxyl, alkoxy, halogen, amino, aminoalkyl, thiol, thioalkyl, carbonyl, phosphonyl, phosphoryl, sulfonyl, sulfinyl; wherein each of $R^1$, $R^2$, $R^3$, and $R^4$ is unsubstituted or substituted by one or more substituents; and wherein m is 0 to 7.

In another embodiment, the invention provides a method for producing a compound of formula (I), (II), or (III), the method comprising: adding nitrogen to a reaction vessel comprising a thiol, a base, and a nickel salt; adding substantially pure oxygen to the reaction vessel after the nitrogen has been added; heating the reaction vessel; maintaining oxygen at the same pressure during reaction; wherein oxygen is added and maintained at a pressure less than the pressure of nitrogen.

DETAILED DESCRIPTION OF THE INVENTION

The following definitions are provided to determine how terms used in this application, and in particular, how the claims are to be construed. The organization of the definitions is for convenience only and is not intended to limit any of the definitions to any particular category.

The term "substituent," as used herein, is intended to mean a chemical group. Substituents include, but are not limited to halogen, halosubstituted alkyl, alkyl, alkenyl, alkynyl, hydroxyl, oxo, thiol, alkylthio, alkoxy, aryl or heteroaryl, aryloxy or heteroaryloxy, aralkyl or heteroaralkyl, aralkoxy or heteroaralkoxy, HO—(C═O)—, heterocyclic, cycloalkyl, amino, aminoalkyl, alkyl- and dialkylamino, carbonyl, carbamoyl, alkylcarbonyl, alkoxycarbonyl, alkylaminocarbonyl, dialkylamino carbonyl, arylcarbonyl, aryloxycarbonyl, alkylsulfonyl, arylsulfonyl, phosphoryl, phosphonyl, nitro, and cyano. Those skilled in the art will appreciate that many substituents can include additional substituents.

"Alkyl" refers to a straight-chain or branched alkyl, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons. Examples of such alkyl groups include methyl, ethyl, propyl, isopropyl, n-butyl, sec-butyl, isobutyl, tert-butyl, pentyl, isoamyl, hexyl, and the like. Alkyl groups may be unsubstituted or substituted, as defined above.

"Alkenyl" refers to a straight or branched hydrocarbon, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

"Alkylheteroaryl" refers to an alkyl group linked to a heteroaryl group. Heteroaryl group and alkyl group may be unsubstituted or substituted by one or more suitable substituents, as defined above.

"Alkynyl" refers to a straight or branched hydrocarbon, preferably having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above.

"Alkoxy" refers to a moiety of the formula RO—. Alkoxy groups may be unsubstituted or substituted, as defined above.

"Alkylthio" refers to a moiety of the formula RS—. Alkylthio groups may be unsubstituted or substituted, as defined above.

"Amino" refers to the moiety $H_2N$—.

"Aminoalkyl" refers to a nitrogen substituent attached to one or more carbon groups. For example, the aminoalkyl group can be RHN— (secondary) or $R_2N$— (tertiary) where R is alkyl or aryl. Aminoalkyl groups may be unsubstituted or substituted, as defined above.

"Aryl" refers to an unsubstituted or substituted aromatic carbocyclic substituent, as commonly understood in the art, and the term "$C_6$-$C_{10}$ aryl" includes phenyl, naphthyl, and anthracyl, indanyl, and the like. It is understood that the term aryl applies to cyclic substituents that are planar and comprise 4n+2n electrons, according to Hückel's Rule. Aryl groups may be unsubstituted or substituted by one or more suitable substituents, as defined above.

"Carbonyl" refers to a substituent comprising a carbon double bonded to an oxygen. Examples of such substituents include aldehydes, ketones, carboxylic acids, esters, amides, and carbamates. Carbonyl groups may be unsubstituted or substituted by one or more suitable substituents, as defined above.

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. Cycloalkyl groups may be unsubstituted or substituted by one or more suitable substituents, as defined above.

"Dithioalkanol" refers to a disulfide compound substituted with at least one hydroxyl group.

"Dithiocarboxylic acid" refers to a disulfide compound substituted with at least one carboxylic acid.

"Halogen" or "halo" refers to any one or more of fluorine, chlorine, bromine, and iodine.

"Halosubstituted alkyl" refers to an alkyl group as described above substituted with one or more halogens, which may be the same or different, for example, chloromethyl, trifluoromethyl, 2,2,2-trichloroethyl, and the like. Halosubstituted alkyl groups may be unsubstituted or substituted, as defined above.

"Heteroaryl" refers to a monocyclic or bicyclic 5- or 6-membered ring system, wherein the heteroaryl group is unsaturated and satisfies Hückel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like. Heteroaryl groups may be unsubstituted or substituted, as defined above.

"Heterocycle" refers to a monocyclic, bicyclic, or tricyclic group containing 1 to 4 heteroatoms selected from O, N, and S. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, as defined above.

"Hydroxyl" refers to a moiety of the formula HO—.

Whenever a range of the number of atoms in a structure is indicated (e.g., a $C_1$-$C_{32}$ alkyl, $C_2$-$C_{32}$ alkenyl, $C_2$-$C_{32}$ alkynyl, etc.), it is specifically contemplated that the substituent can be described by any of the carbon atoms in the sub-range or by any individual number of carbon atoms falling within the indicated range. By way of example, a description of the group such as an alkyl group using the recitation of a range of 1-32 carbon atoms (e.g., $C_1$-$C_{32}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-32 carbon atoms (e.g., $C_2$-$C_{32}$) encompasses and specifically describes an alkyl group having any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 and 32 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-13 carbon atoms, 1-14 carbon atoms, 1-15 carbon atoms, 1-16 carbon atoms, 1-17 carbon atoms, 1-18 carbon atoms, 1-19 carbon atoms, 1-20 carbon atoms, 1-21 carbon atoms, 1-22 carbon atoms, 1-23 carbon atoms, 1-24 carbon atoms, 1-25 carbon atoms, 1-26 carbon atoms, 1-27 carbon atoms, 1-28 carbon atoms, 1-29 carbon atoms, 1-30 carbon atoms, 1-31 carbon atoms, 1-32 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-13 carbon atoms, 2-14 carbon atoms, 2-15 carbon atoms, 2-16 carbon atoms, 2-17 carbon atoms, 2-18 carbon atoms, 2-19 carbon atoms, 2-20 carbon atoms, 2-21 carbon atoms, 2-22 carbon atoms, 2-23 carbon atoms, 2-24 carbon atoms, 2-25 carbon atoms, 2-26 carbon atoms, 2-27 carbon atoms, 2-28 carbon atoms, 2-29 carbon atoms, 2-30 carbon atoms, 2-31 carbon atoms, 2-32 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 3-13 carbon atoms, 3-14 carbon atoms, 3-15 carbon atoms, 3-16 carbon atoms, 3-17 carbon atoms, 3-18 carbon atoms, 3-19 carbon atoms, 3-20 carbon atoms, 3-21 carbon atoms, 3-22 carbon atoms, 3-23 carbon atoms, 3-24 carbon atoms, 3-25 carbon atoms, 3-26 carbon atoms, 3-27 carbon atoms, 3-28 carbon atoms, 3-29 carbon atoms, 3-30 carbon atoms, 3-31 carbon atoms, and/or 3-32 carbon atoms, as appropriate).

Applicants have discovered metal salts that are effective catalysts for oxidative coupling reactions of thiols. In particular, it has been discovered that an oxidative coupling process comprising a nickel salt in the presence of a base catalyst requires very low nickel catalyst loadings to provide complete conversion of thiols to corresponding disulfides with excellent selectivity and short reaction times. It was surprisingly and unexpectedly discovered that organic disulfides can be obtained in high yield using nickel salts with loadings as low as 0.000035% in as little as 4 hours. Thus, the present invention provides a highly economic method of producing thiols of high purity. The reaction generally goes to full completion, and provides disulfides having little to no detectable impurities. Moreover, the efficiency and selectivity of the oxidative coupling reaction of the present invention requires little to no purification or workup. The oxidative coupling of the present invention provides disulfide compounds and salts thereof. In certain embodiments, the oxidative coupling is performed using nickel sulfate or nickel acetate and trialkanolamines or triethylamine as co-catalysts. In certain embodiments, the oxidative coupling reaction forms a dithioalkanol or a dithiocarboxylic acid.

The oxidative coupling reaction can be an intermolecular reaction or an intramolecular reaction. Oxidative coupling can occur between two thiol molecules, which may be the same or different. Oxidative coupling can occur between two thiols in the same molecule. Thiols of the present invention can be of any type, including substituted or unsubstituted alkyl, alkenyl, alkynyl, aryl, and heteroaryl thiols. The thiols of the present invention can be linear or branched.

In an embodiment, the invention provides a method for producing a compound of formula (I)

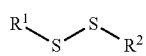

(I)

or a salt thereof, the method comprising contacting a thiol and a nickel salt, in the presence of a base, with oxygen; wherein each of $R^1$ and $R^2$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, or wherein $R^1$ and $R^2$ form a carbocyclic or heterocyclic ring; and wherein each of $R^1$ and $R^2$ is unsubstituted or substituted by one or more substituents.

The $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, carbonyl, halosubstituted alkyl groups, and carbocyclic or heterocyclic ring formed from $R^1$ and $R^2$ each can be independently substituted with any suitable organic substituent. In certain embodiments, each of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, carbonyl, halosubstituted alkyl groups and/or carbocyclic or heterocyclic ring formed from $R^1$ and $R^2$ are independently substituted with one or more substituents selected from the group consisting of halogen, halosubstituted alkyl, alkyl, alkenyl, alkynyl, hydroxyl, oxo, thiol, alkylthio, alkoxy, aryl or heteroaryl, aryloxy or heteroaryloxy, aralkyl or heteroaralkyl, aralkoxy or heteroaralkoxy, HO—(C═O)—, heterocyclic, cycloalkyl, amino, aminoalkyl, alkyl- and dialkylamino, carbonyl, carbamoyl, alkylcarbonyl, alkoxycarbonyl, alkylaminocarbonyl, dialkylamino carbonyl, arylcarbonyl, aryloxycarbonyl, alkyl sulfonyl, arylsulfonyl, phosphoryl, phosphonyl, nitro, and cyano.

In certain embodiments, $R^1$ and $R^2$ are $C_1$-$C_{32}$ alkyl. In certain embodiments, $R^1$ and $R^2$ are each selected from $C_1$-$C_{10}$-alkyl (e.g., methyl, ethyl, propyl (e.g., n-propyl, isopropyl), butyl (e.g., n-butyl, isobutyl, tert-butyl, sec-butyl), pentyl (e.g., n-pentyl, isopentyl, tert-pentyl, neopentyl, sec-pentyl, 3-pentyl), hexyl, heptyl, octyl, nonyl, or decyl), each independently substituted with 1 to 3 substituents independently selected from the group consisting of halogen, halosubstituted alkyl, alkyl, alkenyl, alkynyl, hydroxyl, oxo, thiol, alkylthio, alkoxy, aryl or heteroaryl, aryloxy or heteroaryloxy, aralkyl or heteroaralkyl, aralkoxy or heteroaralkoxy, HO—(C═O)—, heterocyclic, cycloalkyl, amino, aminoalkyl, alkyl- and dialkylamino, carbonyl, carbamoyl, alkylcarbonyl, alkoxycarbonyl, alkylaminocarbonyl, dialkylamino carbonyl, arylcarbonyl, aryloxycarbonyl, alkyl sulfonyl, arylsulfonyl, phosphoryl, phosphonyl, nitro, and cyano.

In certain embodiments, $R^1$ and $R^2$ are $C_1$-$C_{10}$ alkyl.

In certain embodiments, the compound of formula (I) is

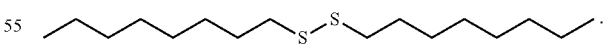

In certain embodiments, $R^1$ and $R^2$ are each selected from $C_6$-$C_{12}$ aryl (e.g., phenyl, dihydroindenyl, indenyl, naphthyl, dihydronaphthalenyl, or 5,6,7,8-tetrahydronaphthalenyl), each substituted with 1 to 5 substituents independently selected from the group consisting of —OH, —NH$_2$, and —COOH.

In certain embodiments, the compound of formula (I) is selected from the group consisting of 4-aminophenyl disulfide; 2-aminophenyl disulfide; and 2,2'-dithiodipyridine.

In certain embodiments, the compound of formula (I) is

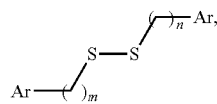

wherein each Ar is the same or different and is aryl, and wherein each of m and n is the same or different and is an integer from 1 to 12.

In certain embodiments, the compound of formula (I) is

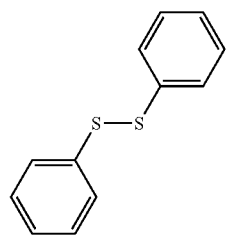

In certain embodiments, the compound of formula (I) is

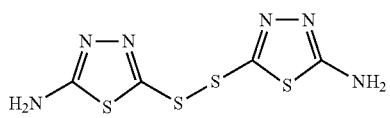

or a salt thereof.

In certain embodiments, the compound of formula (I) is

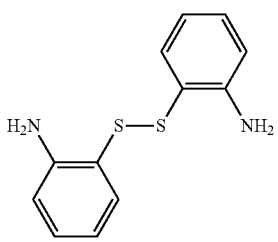 [SMILES: Nc1ccccc1SSc1ccccc1N]

or a salt thereof.

In certain embodiments, the compound of formula (I) is

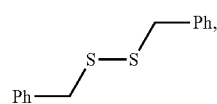

wherein Ph is phenyl.

In certain embodiments, the invention provides a compound of formula (I) or a salt thereof produced by contacting a thiol and a nickel salt, in the presence of a base, with oxygen,

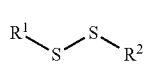

(I)

wherein each of $R^1$ and $R^2$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, or wherein $R^1$ and $R^2$ form a carbocyclic or heterocyclic ring; and wherein each of $R^1$ and $R^2$ is unsubstituted or substituted by one or more substituents.

In another embodiment, the invention provides a method for producing a compound of formula (II)

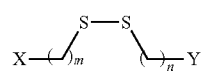

(II)

or a salt thereof,
the method comprising contacting a thiol and a nickel salt, in the presence of a base, with oxygen; wherein each of X and Y is the same or different and selected from the group consisting of —OH, —SH, —NH$_2$, halogen, —COOH, and —COOR; and wherein each of m and n is the same or different and is an integer from 1 to 16, and wherein R is $C_1$-$C_{18}$ alkyl or aryl. The compound of formula (II) may be unsubstituted or further substituted with one or more substituents.

In certain embodiments, the oxidative coupling reaction forms a dithioalkanol or dithiocarboxylic acid. In certain embodiments, the compound of formula (II) is selected from the group consisting of 2,2'-dithiodiethanol; 2,2'-dithiodiacetic acid; 3,3'-dithiodipropionic acid; 4,4'-dithiodibutyric acid; and 3,3'-dihydroxydiphenyl disulfide.

In certain embodiments, the compound of formula (II) is

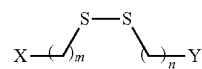

or a salt thereof, wherein each of X and Y is the same or different and selected from the group consisting of —OH, —SH, —NH$_2$, halogen, and —COOH; and wherein each of m and n is the same or different and is an integer from 1 to 6.

In certain embodiments, the compound of formula (II) is

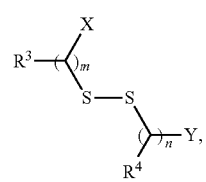

wherein each of $R^3$ and $R^4$ are the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, carbonyl, and halosubstituted alkyl or wherein $R^3$ and $R^4$ forms a ring; wherein each of $R^3$ and $R^4$ is unsubstituted or substituted by one or more substituents; wherein each of X and Y is the same or different and is selected from the group consisting of —OH, —SH, —NH$_2$, halogen, and —COOH; and wherein each of m and n is the same or different and is an integer from 1 to 12.

In certain embodiments, the compound of formula (II) is

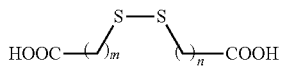

or a salt thereof, wherein each of m and n is the same or different, and is an integer from 1 to 12.

In certain embodiments, the compound of formula (II) is

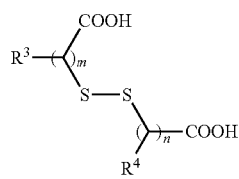

or a salt thereof, wherein each of $R^3$ and $R^4$ are the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, carbonyl, and halosubstituted alkyl or wherein $R^3$ and $R^4$ forms a ring; wherein each of $R^3$ and $R^4$ is unsubstituted or substituted by one or more substituents; and wherein each of m and n is the same or different and is an integer from 1 to 12.

In certain embodiments, the compound of formula (II) is

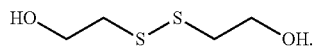

In certain embodiments, the compound of formula (II) is

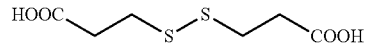

or a salt thereof.

In certain embodiments, the compound of formula (II) is

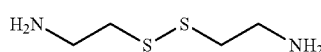

or a salt thereof.

In certain embodiments, the compound of formula (II) is

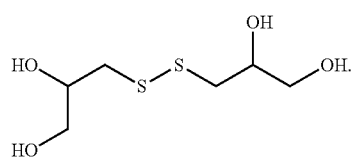

In certain embodiments, the compound of formula (II) is

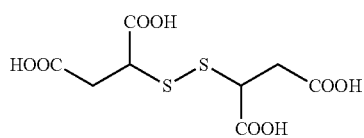 [SMILES: O=C(O)CC(SSC(CC(=O)O)C(=O)O)C(=O)O]

or a salt thereof.

In certain embodiments, the compound of formula (II) is

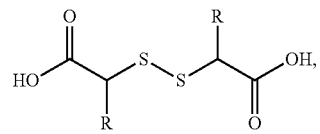

wherein R is hydrogen, hydroxyl, amino, aminoalkyl, $C_1$-$C_{32}$ alkyl, or aryl.

In certain embodiments, the compound of formula (II) is

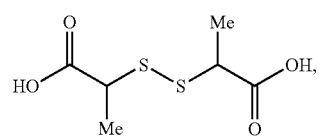

wherein Me is methyl.

In certain embodiments, the compound of formula (II) is

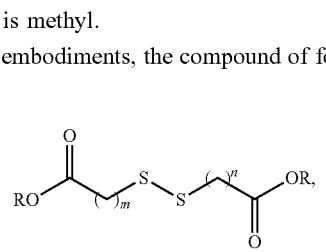

wherein R is $C_1$-$C_{10}$ alkyl or aryl, and wherein each m and n is the same or different and is 1 or 2.

In certain embodiments, the compound of formula (II) is

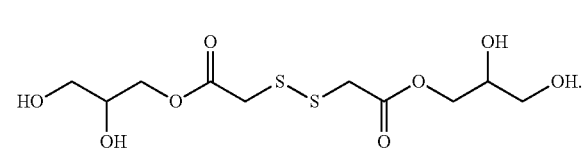 [SMILES: O=C(CSSCC(=O)OCC(O)CO)OCC(O)CO]

In certain embodiments, the compound of formula (II) is

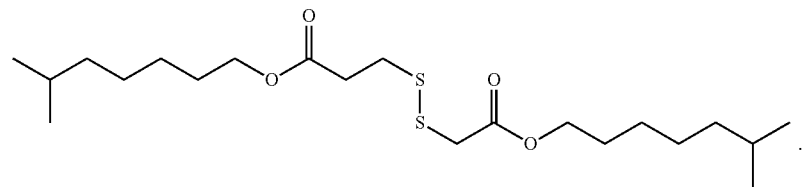 [SMILES: CC(C)CCCCCOC(=O)CCSSCC(=O)OCCCCCC(C)C]

In certain embodiments, the compound of formula (II) is

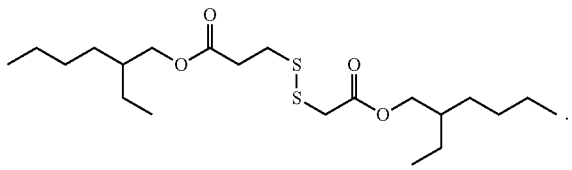 [SMILES: CCCCC(CC)COC(=O)CCSSCC(=O)OCC(CC)CCCC]

In certain embodiment, the compound of formula (II) is

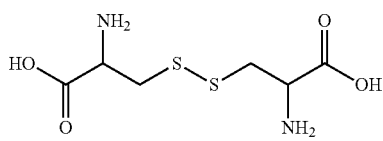 [SMILES: NC(CSSCC(N)C(=O)O)C(=O)O]

or a salt thereof.

In certain embodiments, the invention provides a compound of formula (II) or a salt thereof produced by contacting a thiol and a nickel salt, in the presence of a base, with oxygen,

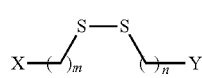
(II)

wherein each of X and Y is the same or different and selected from the group consisting of —OH, —SH, —NH$_2$, halogen, —COOH, and —COOR; and wherein each of m and n is the same or different and is an integer from 1 to 16, R is $C_1$-$C_{18}$ alkyl or aryl, and wherein the compound of formula (II) is unsubstituted or substituted by one or more substituents.

In another embodiment, the invention provides a method for producing a cyclic compound of formula (III)

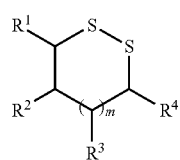
(III)

or a salt thereof, the method comprising contacting a thiol and a nickel salt, in the presence of a base, with oxygen; wherein each of $R^1$, $R^2$, $R^3$, and $R^4$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, hydroxyl, alkoxy, halogen, amino, aminoalkyl, thiol, thioalkyl, carbonyl, phosphonyl, phosphoryl, sulfonyl, sulfinyl; wherein each of $R^1$, $R^2$, $R^3$, and $R^4$ is unsubstituted or substituted by one or more substituents; and wherein m is 0 to 7.

In certain embodiments, the compound of formula (III) is

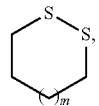

wherein m is 0 to 7.

In certain embodiments, the compound of formula (III) is

In certain embodiments, the compound of formula (III) is

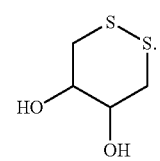

In certain embodiments, a compound of formula (III) may be mixed with

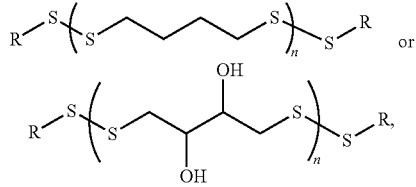

wherein R is $C_1$-$C_{32}$ alkyl or aryl and wherein n is 1.

In certain embodiments, the invention provides a compound of formula (III) or a salt thereof produced by contacting a thiol and a nickel salt, in the presence of a base, with oxygen, $$\text{(III)}$$

wherein each of $R^1$, $R^2$, $R^3$, and $R^4$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, hydroxyl, alkoxy, halogen, amino, aminoalkyl, thiol, thioalkyl, carbonyl, phosphonyl, phosphoryl, sulfonyl, sulfinyl; wherein each of $R^1$, $R^2$, $R^3$, and $R^4$ is unsubstituted or substituted by one or more substituents; and wherein m is 0 to 7.

The method for producing a compound of formula (III) can occur via intramolecular oxidative coupling of a thiol compound having more than one sulfur atom. The oxidative coupling reaction may produce a mixture of a compound of formula (III) and product or products formed from an intermolecular oxidative coupling reaction. In certain embodiments, the oxidative coupling method produces a greater amount of a compound of formula (III) than product or products resulting from an intermolecular oxidative coupling reaction. In certain embodiments, the oxidative coupling method produces a disulfide of formula (III) with formation of little to no side products (e.g., little to no intermolecular oxidative coupling product).

The compounds of the present invention may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

The compounds of the present invention may exist as any suitable salt, including but not limited to, ammonium salts or metal salts.

The oxidative coupling reaction of the present invention can be performed using any suitable metal. Transition metal salts of period 4 and group 10 of the periodic table act as catalysts in the oxidative coupling reaction. Applicants have discovered that nickel salts are particularly useful. In certain embodiments, the nickel salt is selected from the group consisting of nickel sulfate, nickel acetate, nickel chloride, nickel bromide, nickel iodide, nickel fluoride, nickel perchlorate, nickel phosphate, nickel nitrate, nickel nitrite, nickel hydroxide, nickel carbonate, nickel acetylacetonate, nickel titanate, nickel hydroxide, and combinations thereof. In certain embodiments, the nickel salt is nickel sulfate or nickel acetate. In certain other embodiments, the oxidative coupling reaction is performed using a zinc, titanium, vanadium, palladium, platinum, or scandium salt or complex.

The nickel salt can be used in any suitable amount. In certain embodiments, the molar ratio of nickel salt to thiol is about 0.0005 to 1 or less. Thus, in certain embodiments, the molar ratio of nickel salt to thiol is about 0.0005 to 1 or less, about 0.0004 to 1 or less, about 0.0003 to 1 or less, about 0.00025 to 1 or less, about 0.0002 to 1 or less, about 0.0001 to 1 or less, about 0.00009 to 1 or less, about 0.00008 to 1 or less, about 0.000075 to 1 or less, about 0.00007 to 1 or less, about 0.00006 to 1 or less, about 0.00005 to 1 or less, about 0.00004 to 1 or less, about 0.000035 to 1 or less, about 0.00003 to 1 or less, about 0.000025 to 1 or less, about 0.00002 to 1 or less, or about 0.00001 to 1 or less.

Oxidative coupling is performed in the presence of oxygen. In certain embodiments, the oxidative coupling reaction is performed in the presence of substantially pure oxygen. In certain embodiments, the oxidative coupling reaction is performed in the presence of a mixture of oxygen and an inert gas. In certain embodiments, the oxidative coupling reaction is performed in the presence of a mixture of oxygen and nitrogen. In certain embodiments, the oxidative coupling reaction is performed in the presence of a mixture of oxygen and argon. In certain embodiments, the nitrogen pressure is greater than the oxygen pressure. In certain embodiments, the oxidative coupling reaction is performed in the presence of air.

The pressure at which the oxidative coupling reaction takes place is not narrowly critical to the method of the present invention. In certain embodiments, the reaction pressure is of from about 100 psig to about 500 psig. Thus, in certain embodiments, the reaction pressure is of from about 100 psig to about 500 psig, from about 100 psig to about 450 psig, from about 100 psig to about 400 psig, from about 100 psig to about 350 psig, from about 100 psig to about 300 psig, from about 100 psig to about 250 psig, from about 100 psig to about 200 psig, from about 100 psig to about 150 psig, from about 150 psig to about 500 psig, from about 150 psig to about 450 psig, from about 150 psig to about 400 psig, from about 150 psig to about 350 psig, from about 150 psig to about 300 psig, from about 150 psig to about 250 psig, from about 150 psig to about 200 psig, from about 200 psig to about 500 psig, from about 200 psig to about 450 psig, from about 200 psig to about 400 psig, from about 200 psig to about 350 psig, from about 200 psig to about 300 psig, from about 200 psig to about 250 psig, from about 250 psig to about 500 psig, from about 250 psig to about 450 psig, from about 250 psig to about 400 psig, from about 250 psig to about 350 psig, from about 250 psig to about 300 psig, from about 300 psig to about 500 psig, from about 300 psig to about 450 psig, from about 300 psig to about 400 psig, from about 300 psig to about 350 psig, from about 350 psig to about 500 psig, from about 350 psig to about 450 psig, from about 350 psig to about 400 psig, from about 400 psig to about 500 psig, or from about 400 psig to about 450 psig.

The reaction can be conducted with molecular oxygen in any physical form. In certain embodiments, the molecular oxygen is in gas form. In certain embodiments, the molecular oxygen is in liquid form.

In certain embodiments, the oxidative coupling reaction is carried out in the presence of a base. The base is an organic base or an inorganic base. In certain other embodiments, the oxidative coupling is carried-out in the absence of a base.

In certain embodiments, the organic base is triethanolamine, triethylamine, triisopropylamine, trimethylamine, tripropylamine, tributylamine, triamylamine, triphenylamine, ethyldimethylamine, diethanolamine, diethylamine, diisopropylamine, dimethylamine, dipropylamine, dibutylamine, diamylamine, diphenylamine, methylpropylamine, piperidine, pyrrolidine, morpholine, pyridine, tert-butylamine, aniline, methylamine, ethylamine, propylamine, isopropylamine, butylamine, amylamine, hexylamine, cyclohexylamine, octylamine, and combinations thereof.

Applicants have discovered that oxidative coupling reactions conducted in the presence of a tertiary amine provides substantially pure disulfide product. In certain embodiments, the organic base is triethylamine. In certain embodiments, the organic base is a trialkanolamine. In certain embodiments, the trialkanolamine is triethanolamine.

In certain embodiments, the oxidative coupling reaction is carried out in the presence of an inorganic base. Nonlimiting examples of inorganic bases include sodium hydroxide, potassium hydroxide, rubidium hydroxide, lithium hydroxide, ammonium hydroxide, magnesium hydroxide, barium hydroxide, calcium hydroxide, sodium carbonate, potassium carbonate, calcium carbonate, strontium carbonate, barium carbonate, magnesium oxide, and combinations thereof. In certain embodiments, the inorganic base is sodium hydroxide. In certain embodiments, the inorganic base is ammonium hydroxide.

The base can be used in any suitable amount. In certain embodiments, thiol and base is combined at a molar ratio of less than about 1 to 0.05. Thus, in certain embodiments, the molar ratio of base to thiol is about 0.05 to 1 or less, about 0.04 to 1 or less, about 0.03 to 1 or less, about 0.025 to 1 or less, about 0.02 to 1 or less, about 0.01 to 1 or less, about 0.0075 to 1 or less, about 0.005 to 1 or less, about 0.0025 to 1 or less, or about 0.001 to 1 or less.

While it well known that oxidative coupling reactions of thiols can occur in the presence of oxygen and base without metal catalyst, Applicants have discovered that the present method of using a metal salt provides a faster reaction requiring lower temperatures and pressures in comparison to oxidative coupling reactions in the absence of a metal salt. Lower temperatures, pressures, and faster reactions times are essential to providing an efficient and cost-effective means of manufacturing disulfide compounds.

The oxidative coupling reaction can be performed in the absence or presence of a solvent. In certain embodiments, when the starting materials are liquids, the oxidative coupling reaction is performed in the absence of solvent. In certain embodiments, the oxidative coupling reaction is performed in the presence of water. In certain embodiments, the oxidative coupling reaction is performed in the presence of an organic solvent. Nonlimiting examples of organic solvents include ethanol, methanol, isopropanol, dimethylsulfoxide, acetone, ethyl acetate, diethylether, ethylmethylether, acetonitrile, dimethylformamide, tetrahydrofuran, formic acid, acetic acid, nitromethane, n-butanol, dichloromethane, chloroform, dioxane, toluene, benzene, and combinations thereof.

The oxidative coupling reaction can be performed at any suitable temperature. In certain embodiments, the oxidative coupling reaction is performed at a temperature of less than about 150° C. Thus, the oxidative coupling reaction is performed at a temperature of less than about 150° C., temperature of less than about 140° C., temperature of less than about 130° C., temperature of less than about 120° C., less than about 115° C., less than about 110° C., less than about 105° C., less than about 100° C., less than about 95° C., less than about 90° C., less than about 85° C., less than about 80° C., less than about 75° C., less than about 70° C., less than about 65° C., less than about 60° C., less than about 55° C., less than about 50° C., less than about 45° C., less than about 40° C., less than about 35° C., less than about 30° C., or less than about 25° C.

An advantage of the present invention is that the oxidative coupling reaction can yield a disulfide in full conversion in as little as about four hours or less. The reaction time will depend upon the reaction conditions, including the temperature, oxygen pressure, base and nickel catalyst loading, and concentration of thiol. While the reaction may take any suitable amount of time, in certain embodiments, the oxidative coupling reaction reaches full conversion at about 20 hours or less, at about 18 hours or less, at about 16 hours or less, at about 15 hours or less, at about 14 hours or less, at about 12 hours or less, at about 10 hours or less, at about 8 hours or less, at about 6 hours or less, or at about 4 hours or less.

An advantage of the present invention is that the disulfide is generated with the formation of little to no side products. In particular, the disulfide is obtained with little to no overoxidation impurities (e.g., thiosulfinates, thiosulfonates, and sulfonic acids). Thus, in certain embodiments, the overoxidation product is present in the disulfide reaction product in amount of less than about 2%, less than about 1.5%, less than about 1%, less than about 0.5%, less than about 0.4%, less than about 0.3%, less than about 0.2%, less than about 0.1%, less than about 0.05%, less than about 0.02%, less than about 0.01%, or less than about 0.001%.

Another advantage of the oxidative coupling of the present invention is that thiol is effectively converted to the disulfide. While the thiol can be converted to disulfide in any amount, in certain embodiments, about 75% or more, about 80% or more, about 85% or more, about 90% or more, about 95% or more, about 96% or more, about 97% or more, about 98% or more, about 99% or more, about 99.5% or more, about 99.9% or more, or about 99.99% or more of the thiol is converted to the disulfide.

In certain embodiments, the thiol is present in the disulfide reaction product in an amount of less than about 15%, less than about 10%, less than about 9%, less than about 8%, less than about 7%, less than about 6%, less than about 5%, less than about 4%, less than about 3%, less than about 2%, less than about 1%, less than about 0.5%, less than about 0.2%, less than about 0.1%, less than about 0.01%, or less than about 0.001%.

In certain embodiments, substantially pure oxygen is used to oxidize the thiol. In certain embodiments, the reaction mixture (e.g., thiol, nickel salt, and base) is contacted with substantially pure oxygen at a pressure of from about 100 psig to about 200 psig. The reaction mixture is maintained at a temperature of about 80° C. or less, resulting in complete conversion of the thiol to corresponding disulfide in less than 4 hours. Under the aforementioned conditions, a nickel salt catalyst loading of as little as about 0.0001% (e.g., 0.000035%) or less can be used.

In certain embodiments, the reaction mixture (e.g., thiol, nickel salt, and base) is contacted with substantially pure oxygen at a pressure of from about 100 psig to about 200 psig. The reaction mixture is maintained at a temperature of about 50° C. or less, resulting in complete conversion of the thiol to corresponding disulfide in less than 6 hours. Under the aforementioned conditions, a metal salt catalyst loading of about 0.0003% or less can be used.

In another embodiment, the invention provides a method for producing a compound of formula (I), (II), or (III), the method comprising: adding nitrogen to a reaction vessel comprising a thiol, a base, and a nickel salt; adding substantially pure oxygen to the reaction vessel after the nitrogen has been added; heating the reaction vessel; maintaining oxygen at the same pressure during reaction; wherein oxygen is added and maintained at a pressure less than the pressure of nitrogen.

In certain embodiments, an inert gas is added to the reaction vessel resulting in the reaction vessel being under a pressure of from about 300 psig to about 400 psig. After the addition of nitrogen, substantially pure oxygen is added to the reaction vessel at a pressure of from about 50 psig to about 150 psig. During the oxidative coupling reaction, the reaction vessel is maintained under an oxygen pressure of from about 50 psig to about 150 psig. In certain embodiments, the total pressure in the reaction vessel is from about 300 psig to about 450 psig. In certain embodiments, the reaction vessel comprises a greater nitrogen pressure than oxygen pressure during the oxidative coupling reaction. In certain embodiments, the reaction vessel comprises a greater oxygen pressure than nitrogen pressure. The reaction vessel is heated and maintained at a temperature of about 60° C. or less. In certain embodiments, the reaction vessel is heated and maintained at a temperature of about 50° C. or less. After about 15 hours to about 20 hours, the oxidative coupling reaction is generally complete and may be filtered to remove any colored impurities present due to the presence of nickel salts. In certain embodiments, the quantity of nickel salts is generally too small to require any purification.

In another embodiment, the invention provides a method for producing a compound of formula (I), (II), or (III) or a salt thereof, the method comprising contacting a thiol and a lanthanide salt, in the presence of a base, with oxygen.

In embodiments wherein a lanthanide salt is used to produce a compound of formula (I), each of $R^1$ and $R^2$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, or wherein $R^1$ and $R^2$ form a carbocyclic or heterocyclic ring; and wherein each of $R^1$ and $R^2$ is unsubstituted or substituted by one or more substituents.

In embodiments wherein a lanthanide salt is used to produce a compound of formula (II), each of X and Y is the same or different and selected from the group consisting of —OH, —SH, —$NH_2$, halogen, and —COOH; and wherein each of m and n is the same or different and is an integer from 1 to 16. The compound of formula (II) may be unsubstituted or substituted with one or more substituents.

In embodiments wherein a lanthanide salt is used to produce a compound formula (III) or a salt thereof, each of $R^1$, $R^2$, $R^3$, and $R^4$ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, hydroxyl, alkoxy, halogen, amino, aminoalkyl, thiol, thioalkyl, carbonyl, phosphonyl, phosphoryl, sulfonyl, sulfinyl; wherein each of $R^1$, $R^2$, $R^3$, and $R^4$ is unsubstituted or substituted by one or more substituents; and wherein m is 0 to 7.

In certain embodiments, the lanthanide salt is selected from the group consisting of lanthanum salt, cerium salt, europium salt, ytterbium salt, erbium salt, and combinations thereof. In certain embodiments, the lanthanide salt is a cerium salt.

The oxidative coupling reaction of the present invention can be performed using any suitable cerium salt. In certain embodiments, the cerium salt is selected from the group consisting of cerium sulfate, cerium acetate, cerium chloride, cerium bromide, cerium iodide, cerium fluoride, cerium perchlorate, cerium phosphate, cerium nitrate, cerium nitrite, cerium hydroxide, cerium carbonate, cerium acetylacetonate, cerium hydroxide, cerium oxalate, ammonium cerium nitrate, and combinations thereof. In certain embodiments, the cerium salt is cerium sulfate or cerium acetate.

The oxidative coupling reaction can be performed in any suitable container or reaction vessel. In certain embodiments, the oxidative coupling reaction is performed by bubbling oxygen or oxygeneous gas into a container comprising thiol, nickel salt, and base. In certain embodiments, the oxidative coupling reaction is performed in an autoclave.

The following examples further illustrate the invention but, of course, should not be construed as in any way limiting its scope.

Example 1

This Example illustrates a method of synthesizing a disulfide in accordance with an embodiment of the present invention.

A 500 mL autoclave was charged with 2-mercaptoethanol (156.30 g), triethanolamine (2.00 g), and nickel sulfate (0.10 g). The autoclave was pressurized with pure oxygen at 150 psig and stirred at 500 rpm. The reaction mixture was slowly heated and allowed to exotherm to 50-80° C. Samples were taken at one hour intervals and analyzed by both $C^{13}$ NMR and gas chromatography. The reaction was complete in less than 6 hours. The product was darker in color due to nickel salts present, but no other impurities were detected at measurable levels. When nickel acetate was used, the product was obtained with a slightly lighter color. If necessary, the product could be filtered to remove metal salts to lighten the color.

TABLE 1

| Chemical | Molar Equivalent | Component Type |
| --- | --- | --- |
| 2-Mercaptoethanol | 1.00 | Reactant |
| Triethanolamine | 0.01 | Co-catalyst |
| Nickel sulfate | 0.000035 | Co-catalyst |
| Oxygen | — | Oxidant |

Example 2

This Example illustrates a method of synthesis of disulfide in accordance with an embodiment of the present invention.

A 500 mL autoclave was charged with 2-mercaptoethanol (156.30 g), triethanolamine (1.00 g), and nickel sulfate (0.10 g). The autoclave was pressurized with pure oxygen at 150 psig and stirred at 500 rpm. The reaction mixture was slowly heated and allowed to exotherm to 40-50° C. Samples were taken at one hour intervals and analyzed by both $C^{13}$ NMR and gas chromatography. The reaction was complete in less than 8 hours. The product was darker in color due to nickel salts present, but no other impurities were detected at measurable levels. If necessary, the product could be filtered to remove metal salts to lighten the color.

TABLE 2

| Chemical | Molar Equivalent | Component Type |
| --- | --- | --- |
| 2-Mercaptoethanol | 1.00 | Reactant |
| Triethanolamine | 0.005 | Co-catalyst |
| Nickel sulfate | 0.0003 | Co-catalyst |
| Oxygen | — | Oxidant |

Example 3

This Example illustrates a method of synthesis of disulfide in accordance with an embodiment of the present invention.

A 500 mL autoclave was charged with 2-mercaptoethanol (156.30 g), triethanolamine (1.00 g), and nickel sulfate (0.15 g). The autoclave was pressurized with nitrogen to 300-400 psig, and then filled with pure oxygen (below explosion limit) until the total pressure was 350-450 psig. Constant oxygen pressure was maintained to ensure that the oxygen level was the same throughout the run. The reaction mixture was stirred at 500 rpm. The reaction mixture was slowly heated and allowed to exotherm to 40-45° C. The temperature was maintained below 50-60° C. throughout the run. Samples were taken at one hour intervals and analyzed by both $C^{13}$ NMR and gas chromatography. The reaction usually complete in 15-20 hours. The product was darker in color due to nickel salts present, but no other impurities were detected at measurable levels. If necessary, the product could be filtered to remove metal salts to lighten the color.

TABLE 3

| Chemical | Molar Equivalent | Component Type |
| --- | --- | --- |
| 2-Mercaptoethanol | 1.00 | Reactant |
| Triethanolamine | 0.005 | Co-catalyst |
| Nickel sulfate | 0.0005 | Co-catalyst |
| Oxygen | — | Oxidant |
| Nitrogen | — | Spectator Gas |

Example 4

This Example demonstrates the effect of metal salt on the ratio of disulfide to thiol. Accordingly, a 500 mL autoclave was charged with 2-mercaptoethanol, triethylamine (TEA) or an inorganic base, and a metal salt. The autoclave was pressurized with pure oxygen and stirred at 500 rpm for entries 1-8. The autoclave was pressurized with air and stirred at 500 rpm for entry 9. The reaction mixture was heated. Samples were analyzed by $C^{13}$ NMR after 10-16 hours.

TABLE 4

| Entry | Catalyst | Catalyst Loading | Base | Oxygen Pressure (psig) | Temp. (° C.) | Ratio of Disulfide/thiol |
| --- | --- | --- | --- | --- | --- | --- |
| 1 | $Ni(OCOCH_3)_2$ | 0.00017 | TEA | 170 | 40 | No thiol detected |
| 2 | $NiSO_4$ | 0.0001 | TEA | 170 | 40 | 95.3 |
| 3 | $Ni(OCOCH_3)_2$ | 0.00012 | NaOH | 170 | 40 | 92.8 |
| 4 | $NiSO_4$ | 0.0001 | NaOH | 170 | 40 | No thiol detected |
| 5 | $Ni(OCOCH_3)_2$ | 0.00026 | $NH_4OH$ | 160 | 75 | No thiol detected |
| 6 | $NiSO_4$ | 0.00024 | $NH_4OH$ | 160 | 75 | No thiol detected |
| 7 | $Ce(SO_4)_2$ | 0.0001 | TEA | 160 | 70 | 71.2 |
| 8 | $Ce(OCOCH_3)_3$ | 0.000075 | TEA | 170 | 70 | 64.8 |
| 9 | $CoSO_4$ | 0.00011 | TEA | 170 | 70 | 30.9 |
| 10 | $Co(OCOCH_3)_2$ | 0.0001 | TEA | 170 | 70 | 34.9 |
| 11 | $Bi(OCOCH_3)_3$ | 0.0105 | TEA | 200 (air) | 40 | 5.7 |

As shown in Table 4, a greater proportion of disulfide is formed after 10-16 hours in the presence of a nickel salt than in the presence of the corresponding cerium salt and cobalt salt. For example, entry 1 demonstrates that quantitative conversion is obtained when nickel acetate is used as a catalyst. It was also discovered that cerium salts such as cerium sulfate and cerium acetate can be used in an oxidative coupling reaction, producing a moderate to good disulfide to thiol ratio. It was surprisingly and unexpectedly discovered that both nickel salts and cerium salts catalyze the oxidative coupling reaction in a much more facile manner than the corresponding cobalt salts.

Example 5

This Example demonstrates the oxidative metal-catalyzed thiol coupling of various thiols. Accordingly, a 500 mL autoclave was charged with a thiol, triethylamine (TEA), and a metal salt. The autoclave was pressurized with pure oxygen (150 psi) and stirred at 500 rpm. The reaction mixture was heated. Samples were analyzed by $C^{13}$ NMR after 4 hours.

TABLE 5

| Entry | Thiol | Catalyst | Catalyst Conc. (%) | Temp. (° C.) | Ratio of Disulfide/thiol |
| --- | --- | --- | --- | --- | --- |
| 1 | thioglycerol | $NiSO_4$ | 0.001 | 50 | Quantitative |
| 2 | thioglycerol | $Ni(OCOCH_3)_2$ | 0.001 | 50 | Quantitative |
| 3 | benzyl mercaptan | $NiSO_4$ | 0.08 | 70 | 96% |
| 4 | benzyl mercaptan | $Ni(OCOCH_3)_2$ | 0.08 | 70 | 81% |
| 5 | thiophenol | $NiSO_4$ | 0.12 | 70 | Quantitative |
| 6 | thiophenol | $Ni(OCOCH_3)_2$ | 0.12 | 70 | Quantitative |

TABLE 5-continued

| Entry | Thiol | Catalyst | Catalyst Conc. (%) | Temp. (° C.) | Ratio of Disulfide/thiol |
|---|---|---|---|---|---|
| 7 | 3--mercaptopropionic acid | NiSO₄ | 0.09 | 70 | 99% |
| 8 | 3-mercaptopropionic acid | Ni(OCOCH₃)₂ | 0.09 | 70 | 52% |
| 9 | thiolactic acid | NiSO₄ | 0.094 | 70 | 89% |
| 10 | thiolactic acid | Ni(OCOCH₃)₂ | 0.094 | 70 | 76% |
| 11 | mercaptosuccinnic acid | NiSO₄ | 0.175 | 70 | 74% |

As shown in Table 5, a variety of thiols oxidatively couple to form disulfide compounds. Both thioglycerol and thiophenol converted to the corresponding disulfide quantitatively. For certain thiols, a greater proportion of disulfide was formed when nickel sulfate was used as a catalyst.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing a compound of formula (II)

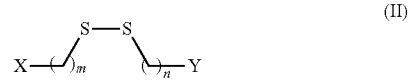

or a salt thereof,
the method comprising contacting a thiol and a nickel salt, in the presence of a base, with oxygen; wherein each of X and Y is the same or different and selected from the group consisting of —OH, —SH, —NH₂, halogen, —COOH, and —COOR; and wherein each of m and n is the same or different and is an integer from 1 to 16, R is $C_1$-$C_{18}$ alkyl or aryl, and wherein the compound of formula (II) is unsubstituted or substituted by one or more substituents.

2. The method of claim 1, wherein the compound of formula (II) is

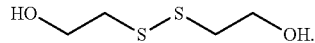

3. The method of claim 1, wherein the compound of formula (II) is

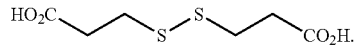

4. The method of claim 1, wherein the compound of formula (II) is

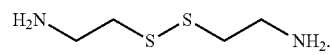

5. The method of claim 1, wherein the nickel salt is selected from the group consisting of nickel sulfate, nickel acetate, and a combination thereof.

6. The method of claim 1, wherein the organic base is a tertiary amine.

7. The method of claim 1, wherein the molar ratio of the nickel salt to thiol is about 0.0005 to 1 or less.

8. A method of producing a compound of formula (I), (II), or (III) or a salt thereof, the method comprising:
adding nitrogen to a reaction vessel comprising a thiol, a base, and a nickel salt;
adding substantially pure oxygen to the reaction vessel after the nitrogen has been added; heating the reaction vessel;

maintaining oxygen at the same pressure during reaction;
wherein oxygen is added and maintained at a pressure less than the pressure of nitrogen, and
wherein formula (I) is

wherein each of R¹ and R² is the same or different, and is selected from the group consisting of $C_1$-$C_{32}$ alkyl, $C_2$-$C_{32}$ alkenyl, $C_2$-$C_{32}$ alkenyl, aryl, heteroaryl, heterocycle, $C_3$-$C_8$ cycloalkyl, benzyl, alkylheteroaryl, and halosubstituted alkyl, or wherein R¹ and R² form a carbocyclic or heterocyclic ring; and wherein each of R¹ and R² is unsubstituted or substituted by one or more substituents, formula (II) is

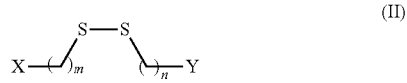

wherein each of X and Y is the same or different and selected from the group consisting of —OH, —SH, —NH₂ halogen, —COOH, and —COOR; and wherein each of m and n is the same or different and is an integer from 1 to 16, R is $C_1$-$C_{18}$ alkyl or aryl, and wherein the compound of formula (II) is unsubstituted or substituted by one or more substituents, and formula (III) is

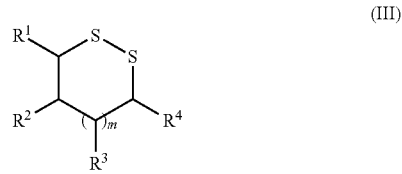

wherein each of R¹, R², R³, and R⁴ is the same or different, and is selected from the group consisting of $C_1$-$C_{32}$ alkyl, $C_2$-$C_{32}$ alkenyl, $C_2$-$C_{32}$ alkynyl, aryl, heteroaryl, heterocycle, $C_3$-$C_8$ cycloalkyl, benzyl, alkylheteroaryl, and halosubstituted alkyl, hydroxyl, alkoxy, halogen, amino, aminoalkyl, thiol, thioalkyl, carbonyl, phosphonyl, phosphoryl, sulfonyl, sulfinyl, wherein each of R¹, R², R³, and R⁴ is unsubstituted or substituted by one or more substituents, and wherein m is 0 to 7.

9. The method of claim 8, wherein the compound of formula (II) is produced and has the formula

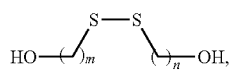

wherein each of m and n is the same or different and is an integer from 1 to 12.

10. The method of claim 8, wherein the compound of formula (II) is produced and has the formula

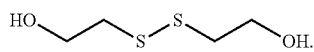

11. The method of claim 8, wherein the compound of formula (II) is produced and has the formula

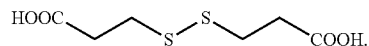 [SMILES: O=C(O)CCSSCCC(=O)O]

12. The method of claim 8, wherein the nickel salt is selected from the group consisting of nickel sulfate, nickel acetate, and a combination thereof.

13. The method of claim 8, wherein the reaction vessel is maintained under an oxygen pressure of from about 50 psig to about 150 psig.

14. The method of claim 8, wherein the reaction vessel is maintained at a temperature of about 60° C. or less.

15. The method of claim 8, wherein the compound of formula (III) is produced and has the formula

wherein m is 0 to 7.

16. The method of claim 8, wherein the compound of formula (III) is produced and has the formula

17. The method of claim 8, wherein the compound of formula (III) is produced and is mixed with

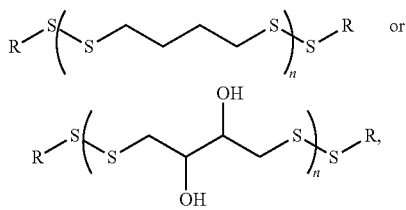

wherein R is $C_1$-$C_{32}$ alkyl or aryl and wherein n is 1.

18. The method of claim 1, wherein the base is an organic base.

19. The method of claim 18, wherein the organic base is selected from triethanolamine, triethylamine, triisopropylamine, trimethylamine, tripropylamine, tributylamine, triamylamine, triphenylamine, ethyldimethylamine, diethanolamine, diethylamine, diisopropylamine, dimethylamine, dipropylamine, dibutylamine, diamylamine, diphenylamine, methylpropylamine, piperidine, pyrrolidine, morpholine, pyridine, tert-butylamine, aniline, methylamine, ethylamine, propylamine, isopropylamine, butylamine, amylamine, hexylamine, cyclohexylamine, octylamine, or a combination thereof.

20. The method of claim 18, wherein the organic base is triethanolamine.

* * * * *

UNITED STATES PATENT AND TRADEMARK OFFICE
CERTIFICATE OF CORRECTION

PATENT NO. : 9,834,509 B2
APPLICATION NO. : 15/228364
DATED : December 5, 2017
INVENTOR(S) : Anantaneni et al.

It is certified that error appears in the above-identified patent and that said Letters Patent is hereby corrected as shown below:

In the Claims

At Column 23, Line 14, please delete "$C_2$-$C_{32}$ alkenyl, aryl" and add --$C_2$-$C_{32}$ alkynyl, aryl--

At Column 23, Lines 53-54, please delete "sulfinyl, wherein" and add --sulfinyl; wherein--

At Column 23, Line 56, please delete "substituents, and" and add --substituents; and--

At Column 25, Line 4, please delete "tert-butylamine" and add --*tert*-butylamine--

Signed and Sealed this
Sixth Day of March, 2018

Andrei Iancu
*Director of the United States Patent and Trademark Office*